United States Patent [19]

Kauvar

[11] Patent Number: 4,963,263

[45] Date of Patent: Oct. 16, 1990

[54] METHOD OF IDENTITY ANALYTE-BINDING PEPTIDES

[75] Inventor: Lawrence M. Kauvar, San Francisco, Calif.

[73] Assignee: Terrapin Technologies, Inc., San Francisco, Calif.

[21] Appl. No.: 355,042

[22] Filed: May 16, 1989

Related U.S. Application Data

[63] Continuation of Ser. No. 172,626, Mar. 24, 1988, abandoned.

[51] Int. Cl.⁵ .............................................. B01D 15/08
[52] U.S. Cl. ................................. 210/635; 210/656; 436/161; 530/413
[58] Field of Search ............ 210/635, 656, 658, 198.2, 210/502.1; 502/400, 401, 402, 403, 404; 530/413; 436/161; 422/70

[56] References Cited

U.S. PATENT DOCUMENTS

| | | | |
|---|---|---|---|
| 4,125,492 | 11/1978 | Cuatrecasas | 210/635 |
| 4,330,440 | 5/1982 | Ayers | 210/635 |
| 4,334,972 | 6/1982 | Soderberg | 210/635 |
| 4,464,165 | 8/1984 | Pollard | 210/635 |
| 4,525,465 | 6/1985 | Someno | 502/403 |
| 4,544,485 | 10/1985 | Pinkerton | 210/656 |
| 4,612,121 | 9/1986 | Hermansson | 210/635 |
| 4,663,163 | 5/1987 | Hou | 210/635 |
| 4,693,985 | 9/1987 | Degen | 210/635 |
| 4,694,044 | 9/1987 | Kiniwa | 210/635 |

FOREIGN PATENT DOCUMENTS

| | | | |
|---|---|---|---|
| 62-278450 | 12/1987 | Japan | 502/403 |
| 62-278451 | 12/1987 | Japan | 502/403 |

OTHER PUBLICATIONS

May et al., in *Separation and Purification*, 3rd Edition, 1978 (Edmond S. Perry et al., eds.), vol. 12, "Techniques of Chemistry" (New York: John Wiley), pp. 257–293.

Peterson et al., (1984), Methods in Enzymology, 104:113–133.

Armstrong et al., (1984), J. Chromatographic Science, 22:411–415.

Atassi et al., (1977), J. Biological Chemistry, 252(24):8784–8787.

McCormick et al., (1984), Biochem. J., 224:995–1000.

Atassi, (1985), Biochem. J., 226:477–485.

Seiden et al., (1986), J. Immunology, 136(2):582–587.

Roux et al., (1987), Proc. Natl. Acad. Sci. (USA), 84:4984–4988.

Takeo et al., (1978), Journal of Immunology, 121(6):2305–2310.

Varga et al., (1974), Journal of Immunology, 112(4):1565–1570.

Janin, (1979), Nature, 277:491–492.

Eisenberg et al., (1984), Proc. Natl. Acad. Sci. (USA), 81:140–144.

Eisenberg et al., (1982), Nature, 299:371–374.

Ohlson, S. et al, *Anal. Biochem.* (1988), 169:204–208.

Fong, G. W-K. et al, *Analytical Chem.* (1978), 50:1154–1161.

Fong, G. W-K. et al, *J. Chromatog.* (1977), 142:299–309.

Shai, Y. et al, *Biochemistry* (1987), 26:699–675.

Primary Examiner—Ernest G. Therkorn
Attorney, Agent, or Firm—Irell & Manella

[57] ABSTRACT

A method for affinity chromatography or adsorption of a designated analyte utilizes a paralog as the affinity partner. The immobilized paralog can be used in purification or analysis of the analyte; the paralog can also be used as a substitute for antibody in an immunoassay. The paralog is identified by screening candidate peptide sequences of 4–20 amino acids for specific affinity to the analyte.

7 Claims, 3 Drawing Sheets

Variation in Hydrophobicity Index and Hydrophobic Moment Across the Panel of Figure 4.

affinity (binding) of analyte

← paralogs → binding of mixture

← paralogs → binding of mixture in presence of analyte

← paralogs →

| # | N-term | 5 | 4 | 3 | C-term | # | N-term | 5 | 4 | 3 | C-term |
|---|---|---|---|---|---|---|---|---|---|---|---|
| 1. | V | A | V | F | A | 49. | G | S | S | S | F |
| 2. | F | G | W | A | I | 50. | G | W | G | K | W |
| 3. | G | A | V | V | F | 51. | W | G | D | G | P |
| 4. | V | V | I | A | P | 52. | N | S | W | G | A |
| 5. | A | A | A | F | F | 53. | S | H | P | G | W |
| 6. | M | V | V | G | W | 54. | S | D | A | A | A |
| 7. | I | G | G | V | A | 55. | A | N | H | A | A |
| 8. | G | F | W | W | M | 56. | D | P | W | S | W |
| 9. | S | I | P | F | I | 57. | W | H | G | P | H |
| 10. | W | V | G | W | A | 58. | S | G | D | P | V |
| 11. | G | P | G | I | F | 59. | H | P | H | G | M |
| 12. | A | F | V | W | S | 60. | S | S | H | A | G |
| 13. | N | V | W | P | W | 61. | G | P | K | A | A |
| 14. | W | I | G | S | W | 62. | H | H | G | S | W |
| 15. | G | A | G | G | F | 63. | A | N | S | S | W |
| 16. | G | M | W | G | W | 64. | S | M | D | S | W |
| 17. | F | V | A | S | G | 65. | A | D | A | N | A |
| 18. | W | G | A | V | P | 66. | G | W | S | D | A |
| 19. | A | S | M | I | A | 67. | N | H | P | G | G |
| 20. | V | A | V | G | S | 68. | M | G | K | A | H |
| 21. | V | F | S | S | V | 69. | N | D | M | S | W |
| 22. | M | W | V | H | W | 70. | A | N | K | M | G |
| 23. | S | V | A | F | P | 71. | G | W | S | N | D |
| 24. | S | A | M | W | W | 72. | G | D | P | D | G |
| 25. | A | W | V | G | H | 73. | H | A | A | N | D |
| 26. | F | W | W | P | H | 74. | S | K | S | G | G |
| 27. | A | M | S | A | W | 75. | D | W | S | W | K |
| 28. | W | A | V | P | S | 76. | A | D | H | N | G |
| 29. | P | G | G | G | W | 77. | G | D | S | G | D |
| 30. | W | W | S | V | S | 78. | S | H | D | P | P |
| 31. | V | D | W | A | A | 79. | P | S | H | K | M |
| 32. | S | G | W | G | M | 80. | S | A | G | D | K |
| 33. | S | W | H | W | G | 81. | D | P | N | A | D |
| 34. | M | W | S | G | P | 82. | M | H | D | S | P |
| 35. | W | A | P | G | S | 83. | P | S | D | D | N |
| 36. | W | D | W | A | G | 84. | D | A | S | D | H |
| 37. | A | I | S | P | S | 85. | H | D | D | S | S |
| 38. | W | S | A | H | W | 86. | G | K | M | D | K |
| 39. | G | S | G | F | H | 87. | D | A | K | S | D |
| 40. | A | A | A | S | S | 88. | S | S | H | D | K |
| 41. | S | S | P | V | A | 89. | S | K | F | W | Y |
| 42. | G | W | S | G | S | 90. | P | L | A | Q | G |
| 43. | W | M | H | S | G | 91. | P | L | A | Q | G |
| 44. | A | S | G | H | W | 92. | G | L | A | Q | G |
| 45. | N | G | M | G | G | 93. | G | L | A | Q | K |
| 46. | W | G | N | P | M | 94. | S | V | N | M | K |
| 47. | P | P | A | S | G | 95. | I | A | H | W | D |
| 48. | G | H | A | S | A | 96. | F | P | K | V | D |

Acetylate N-terminus on all except E12 (for FITC)

Fig. 4

METHOD OF IDENTITY ANALYTE-BINDING PEPTIDES

REFERENCE TO GOVERNMENT SUPPORT

This invention was made with government support under Contract No. DE-AC03-88ER80678 awarded by the Department of Energy. The Government has certain rights in this invention.

This application is a continuation of application Ser. No. 07/172,626, filed 24 March 1988, now abandoned.

TECHNICAL FIELD

The invention relates to chromatographic and analytical methods involving affinity ligands for specific analytes. More particularly, it concerns use of peptide paralogs as affinity ligands in chromatographic techniques for detection and purification of a variety of analytes, in particular toxic contaminants of low immunogenicity. The paralogs may also be employed in immunoassay procedures.

BACKGROUND ART

Two major developments in the practice of chromatographic separations have been of dramatic importance over the last decade or so in facilitating the isolation of natural products, separation of components of mixtures, and analysis of complex compositions. These are the proliferation of the variety of available ligands for affinity chromatography, wherein the separation or analysis depends on the specific interaction between a supported ligand and a desired analyte, and the advent of high performance liquid chromatography (HPLC) which permits rapid and efficient separation of multiple components. These developments have overlapped only to a limited extent, as HPLC generally utilizes conditions which are inimical to many of the legends used as specific affinity partners. The most common affinity partner for use in these techniques with respect to a spectrum of possible analytes has been specific immunoglobulins or immunoreactive fragments thereof. In general, this type of ligand is unstable with respect to the conditions employed in HPLC. HPLC often employs nonaqueous solvents, which are denaturing to many affinity ligands and the high pressures employed are also destructive to many of these substances.

In affinity based chromatography, a variety of solid supports and of affinity ligands can be used, as summarized in an early review article by May, S. W. in *Separation and Purification* 3rd Ed. (1978) Edmond S. Perry, et al, ed., vol. 12 in *Techniques of Chemistry* (J. Wiley). This review describes suitable supports for affinity chromatography emphasizing polysaccharide supports in addition to polyacrylamide gels, mixed gels, and various glasses and silica derivatives. Of these, only silica derivatives have gained wide acceptance for use in HPLC. However, the extent of derivatization of the support to modify its binding characteristics has been limited to altering hydrophobicity by conjugation of various hydrocarbon ligands or other simple molecules.

The present invention enables a convenient crossover between the HPLC and affinity approaches by providing ligands which have the required affinity specific for a selected member of an array of possible analytes with capability to withstand the conditions of HPLC.

Others have attempted this crossover in various ways. Peterson, E. A. et al *Meth Enz* (1984) 104:113–133 describe "displacement" chromatography wherein competition for the adsorption sites between adsorbed components is substituted for competition with eluant. Chromatographic supports which employ carbohydrates, such as cyclodextrins, with differential specific affinities for the substances to be separated have also been reported (Armstrong, D. W. et al *J Chrom Sci* (1984) 22:411–415.

The ligands employed in the invention method are peptides of 4–20 amino acids which are designated "paralogs" herein. A paralog mimics the portion of an immunoglobulin which specifically binds to the antigenic determinant or epitope of the antigen to which the antibody is raised. The segment complementary to this epitope is commonly designated a paratope, and since the peptide sequence in the paralog need not be the same as that occurring in the raised antibodies, the term paralog (or paratope analog) is used.

Synthesis of, and identification of, paralogs has been done previously to a very limited extent. Atassi, M. Z., et al *J Biol Chem* (1977) 252:8784–8787 described the specific design of a peptide complementary to the antigenic sites of lysozyme. Knowledge of the three-dimensional contours of lysozyme permitted the synthesis of a peptide of dimensions and electron density patterns analogous to the deduced determinant. The paralog was obtained by preparing a peptide sequence deliberately complementary in dimension and electron distribution to the determinant-mimicking peptide. The pseudo "paratope" peptides inhibited the reaction of lysozyme with antisera and specifically bound lysozyme to the exclusion of myoglobin or antibody. Later work from the same group resulted in the synthesis of a peptide representing the acetyl choline binding site of a specific receptor and of a binding site in trypsin (McCormick, D. J., et al *Biochem J* (1984) 224:995–1000; Atassi, M. Z. *Biochem J* (1985) 226:477–485). The paralog (or analogous receptor- or enzyme binding site-mimicking) peptides were based on known parameters associated either with the antigenic determinant or with the determinant binding moiety.

Recent work has shown that the idiotypic surface of antibodies can be mapped and peptides mimicking portions of this surface can be prepared. As expected, the idiotopes and paratopes do not precisely coincide. Seiden, M. V. *Am Assoc Immunol* (1986) 136:582–587; Roux, K. H. et al *Proc Natl Acad Sci USA* (1987) 84:4984–4988.

Recently, methods to mimic epitopes as specifically binding complementary components without knowledge of the characteristics of the specific interaction have been disclosed. The most relevant work is that of Geysen, H. M. at the Commonwealth Serum Laboratories in Australia. Geysen has devised an empirical method for preparing a panel of multiple candidate sequences whose ability to bind specifically to antibody can be empirically tested. In the Geysen approach, each of the candidate peptides is separately synthesized on an individual polyethylene support rod in relatively small amount. The support rods are arranged conveniently so as to dip individually into the wells of a microtitre tray. Typically 96 separate peptides can be simultaneously synthesized (the number corresponding to the arrangement of commercially available trays). The 96 peptides can also be simultaneously assayed for binding to antibodies or receptors using standard radioimmunoassay or ELISA techniques. (See, for example, *Proc Natl Acad*

Sci (USA) (1984) 81 3998-4002, PCT applications WO86/00991 and WO86/06487.)

A variety of candidate peptides can also be simultaneously synthesized in separate containers using the T-bag method of Houghten, R., Proc Natl Acad Sci (USA) (1985) 82:5131-5135.

The performance of the paralogs may be improved in some instances by controlling their 3-dimensional conformation through the use of "molecular sticks" as described in U.S. patent application Ser. No. 172,623, filed 24 March 1988, assigned to the same assignee and incorporated herein by reference.

The foregoing elements of the art can be productively used as a resource to construct the ligands needed for the chromatographic substrates and for the conduct of the methods of the herein invention.

DISCLOSURE OF THE INVENTION

The invention provides a useful form of analytical and preparative chromatography on solid supports which permits a combination of the advantages of affinity chromatography and HPLC. By constructing appropriate substrates for chromatographic separations and purifications based on affinity, the procedures can be carried out under efficient conditions which permit ready analysis of components, or their purification or their removal from mixtures. These techniques are particularly useful in removing toxic wastes from effluents, in assaying the quantity of toxins in reservoirs, in analysis of levels of materials at low concentration in the presence of a high concentration of nonspecific contaminants, and in preparative procedures involving HPLC.

Thus, in one aspect, the invention is directed to substrates capable of adsorbing a specified analyte, wherein the substrate comprises a solid support to which is conjugated a ligand consisting essentially of a 4-20 amino acid paralog having specific affinity for the specified analyte. In another aspect, the invention relates to columns or other chromatographic configurations containing this substrate, and to methods of purification and analysis of analytes using these tools.

In still another aspect, the invention is directed to methods to prepare the desired affinity substrates containing paralog ligands; it is also directed to alternate uses for the paralogs, including their substitution for antibodies or fragments thereof in immunoassay procedures. The paralogs may also be used instead of antibodies to screen mimotope panels for members capable of substituting for a particular hapten in the method of pseudo-idiotypic network (PIN) chromatography described in U.S. Ser. No. 108,130, assigned to the same assignee and incorporated herein by reference.

BRIEF DESCRIPTION OF THE DRAWINGS

FIG. 4 shows the panel of 90 candidate pentapeptide paralogs synthesized according to Example 1.

MODES OF CARRYING OUT THE INVENTION

Figure 1:
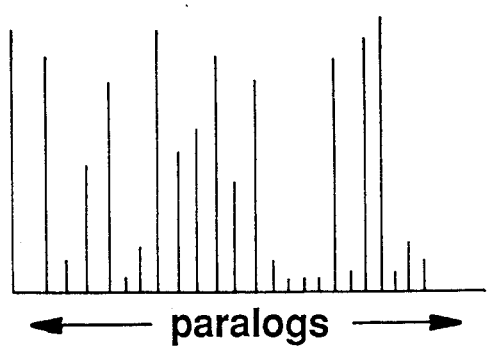
FIG. 1 shows the generic results of a typical ELISA binding assay wherein a panel of paralogs is reacted with a single labeled analyte.

As used herein, "paralog" refers to a peptide having 4-20, preferably 5-15, and more preferably 6-8 amino acids which has specific affinity for a specified analyte or hapten. The paralog mimics the spatial conformation and electron distribution pattern of the paratope region of an antibody which might be raised in response to administration of the analyte. While the paralog can be conceptualized in this manner, it is, of course, not necessary that administration of the analyte, in fact, in every instance (or in any instance) raise immunoglobulins with a paratope of precisely the conformation and pattern of the paralog. It is sufficient that the paralog is capable of exhibiting analogous specific affinity properties with respect to the analyte.

"Specific affinity" refers to the ability of the paralog to bind to the analyte specifically—i.e., the strength of the interaction between analyte and paralog is effectively greater than the strength of the interaction between other materials which might be present with the analyte and the paralog, so that binding to the paralog can be used to distinguish between analyte and "contaminant". Typical values for the specific affinity are of the order of $10^3$ 1/mole to $10^4$ 1/mole at a minimum, and are preferably $10^8$ or $10^{10}$ 1/mole. The needed value is dependent on the environment in which the analyte is found, and on the relative binding strength of the contaminating materials as well as their concentration. In some contexts, a lower affinity is quite adequate, whereas if the paralog also binds strongly to contaminants, especially those present in high concentration, a higher affinity may be required in order to set the binding of the analyte apart from that of contaminants. In short, it is the relative affinity for the analyte in comparison with that for contaminants that is critical. However, the specific affinity should result from the charge/spatial array characteristic of the paralog as complementary to the analyte, rather than from a generalized property such as pI or hydrophobic index.

Methods to measure the affinity of interaction between antigens and high-affinity antibodies is standard; that of interaction with low-affinity antibodies can be measured as described, for example, Takeo, K., et al, J Immunol (1978) 121:2305-2310. Takeo et al describe measurement of binding constants of certain oligosaccharides to specific myeloma proteins using polyacrylamide gel electrophoresis and varying the nature and content of the oligosaccharides in the gel when determining mobilities of the proteins. The method is said to be useful in obtaining binding constants ranging from $10^2$-$10^6$ liters per mole. Varga, J. M., et al, J Immunol (1974) 112:1565-1570, describe the determination of binding constants using nylon-polystyrene whisker discs coupled by glutaraldehyde to immunoglobulins to test the binding of radioactive ligands. Thus, there are a number of protocols in addition to the currently used standard dilution immunoassay procedures in microtiter wells to evaluate binding and quantitate binding constants.

Prepration of Paralogs

The invention is applicable to a wide variety of analytes which may or may not be immunogenic. In addition to analytes which are themselves peptides, and which therefore may permit direct design of paralogs by the "complementarity" approach with regard to sequential overlapping portions of the primary amino acid sequence (a combination of the synthesis/analysis method of Geysen with the complementarity design approach of Atassi) the analytes may be of any origin including drugs such as penicillin, tetracycline, steroids, naproxen, theophylline, vitamins, such as vitamins K, D and A, various toxins such as PCB's, dioxin, and tetrabromoethylene, and any miscellaneous chemical substance having a defined molecular conformation or shape under specified conditions. A specific peptide paralog can be designed for virtually any analyte or a defined region thereof.

The manner of design of the paralog for analytes, whether peptides or nonpeptides, can be approached by a screening procedure among candidate paralog peptides. (This approach can be used, of course, for analytes which are themselves peptides, but the above-mentioned alternative is also available.) In this approach, a panel of candidate paralogs of an arbitrary number of amino acids, typically 4–20, is prepared for screening. It is helpful if the panel can be designed to cover a wide range of electron cloud pattern alternatives so that an approximation of the desired paralog can first be obtained, and subsequent candidates within that range tested for fine tuning.

For example, if paralogs containing 6 amino acids in their primary sequence are employed, there are 64 million possible 6-mers using only the 20 naturally occurring amino acids. Of course, the synthesis of peptides need not be limited to these naturally occurring subunits, and the D-forms of the encoded amino acids as well as various nonencoded amino acids such as beta alanine, amino-butyric acid, citrulline, and the like can also be used. Indeed, these may be preferred as they are expected to be more stable than the "natural" amino acids which are metabolites for microorganisms.

If only a convenient number of such 6-mers are to be synthesized, the parameters which determine electron cloud patterns should be varied widely over the candidates. For example, the prepared candidate peptides should be chosen so that the hydrophobicity index steadily increases across the panel. A discussion of hydrophobicity indices as related to structure is found in Janin, J. *Nature* (1979) 277:491–492. In addition, the amphipathic qualities of the proteins can be varied by adjusting the periodic hydrophobicity of the residues (Eisenberg, D., et al *Proc Natl Acad Sci USA* (1984) 81:140–144; Eisenberg, D., et al *Nature* (1982) 299:371–374). The amphipathic property resides in the secondary or tertiary conformation of the peptide, resulting in portions or faces of the molecule which are water soluble and others which are hydrophobic. In addition, the charge pattern due to the presence of positive or negatively charged amino acid residues can also be varied systematically in the candidate panel.

An initial candidate panel can conveniently consist of about 90 peptides for convenience. This is entirely a reflection of the design of commercially available microtitre plates and protein synthesizer rods (Cambridge Research Biochemicals) and is a convenient number to provide sufficient individual tests to frame the characteristics of the desired paralog. The synthesis is conducted using conventional, usually commercially available, methods, and the panel of individual candidate paralogs is then ready for screening.

Screening Procedures

The screening procedure can be used repeatedly because the binding-based assays used to detect specific affinity are generally reversible so that the testing compositions can subsequently be removed from the paratope panel which remains bound to solid supports. It is not necessary to perform such assays in a recoverable form or bound to solid supports, but it is highly convenient to do so.

The reusability is particularly convenient in the context of one of the intended uses of the paralog—as an affinity ligand in chromatography, since the relative binding strengths in a series of proposed elution solvent systems can be tested systematically. For example, the strength of binding in a series of solutions containing methanol at increasing concentrations or solutions at increasing salt concentrations simulating elution gradients can be used. In this type of testing the comparative behavior of a number of paralogs under a multitude of elution conditions can be tested empirically. This may be very helpful in that the binding constant gradient obtained for paralog X may be preferable to that obtained for paralog Y under desired elution conditions even though paralog Y might appear to have a preferable specific affinity level when tested under only one solvent or temperature condition. The reusability of the test panel thus permits the selection of the best paralog under a pattern of conditions which simulates its use in the chromatographic procedure.

Prior to testing, the paralog panel may or may not be conformation-controlled by linkage to the molecular sticks described in co-pending application docket number 2550-0003 (supra). The entire panel can be treated with the same molecular stick, or by using separate wells, individual molecular sticks may be evaluated across the panel. In such a protocol, it may be useful in some instances to provide multiple pins with the same paralog to be tested with different conformation-controlling molecular stick spacer links.

However the panel is formulated for testing, the panel is then tested for specific affinity of its members to the desired analyte. On a theoretical basis, one might do this directly by labeling the analyte and detecting the relative amount of label bound to the individual paralog members of the panel. Using this approach, a pattern similar to that shown in FIG. 1 will be obtained. As shown in FIG. 1, the amount of label bound to each member of the panel (the y coordinate) is shown across the members of the panel (the x coordinate). Varying amounts of labeling are obtained, depending on the affinity of each paralog for the analyte.

An alternative to this direct method is sometimes more practical. In this alternative, specific affinity is assayed by means of competition of the unlabeled analyte with a mixture of labeled peptides. The peptide mixture must contain a sufficient number of members so that more or less equivalent binding to all paralogs by the labeled mixture per se in the absence of analyte is obtained. This general approach for detecting binding of an unlabeled substance to members of a panel is described in more detail in copending application U.S. Ser. No. 108,130, filed 13 October 1987 and assigned to the same assignee and incorporated herein by reference.

Briefly, the mixture of the requisite number of peptides (roughly on the order of 500–1000, although in some instances smaller members may suffice) is labeled in a suitable manner, for example using the acyl iodination method with the iodine isotope 125 as described by Bolton, A. E., et al, *Biochem J* (1973) 529–539, and available commercially from ICN Radiochemicals. Other labeling methods can also be used. The mixture can be prepared directly by synthesis of individual members and mixing them together or, more conveniently, can be obtained by hydrolysis of large proteins into random small peptides. One approach, for example, utilizes a partial trypsin hydrolysate (Cleveland, D. W., et al *J Biol Chem* (1977) 252:1102–1106) . of a yeast lysate. This provides a large number of peptides which can be labeled as a mixture, or which can be separated using, for example, SDS gel electrophoresis and transferred to a test support such as Immunodyne (Burnette, W. N. *Anal Biochem* (1981) 112:195–203 if their binding is to be assessed individually.

Figure 2:
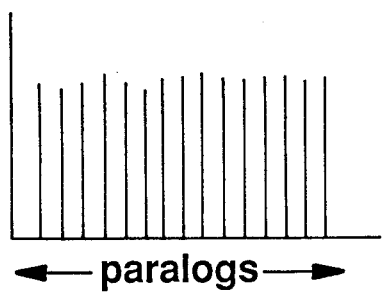
FIG. 2 shows the generic results of a typical ELISA binding assay wherein a panel of paralogs is reacted with a mixture of labeled peptides.

It may be necessary in utilizing the labeled peptide mixture to verify that satisfactory binding occurs with regard to all candidate paralogs in the panel. The conditions for effecting this equivalent binding throughout the panel should also be established empirically. In a perfect situation, the peptide mixture will bind uniformly to all panel members as shown in FIG. 2A. However, more frequently, only similar levels of binding are found, as in FIG. 2B. This provides a perfectly workable basis for competition with analyte. Interpretation of results when competition is added can be simplified by normalization of the binding values to the same value before evaluating the competition.

Figure 3:
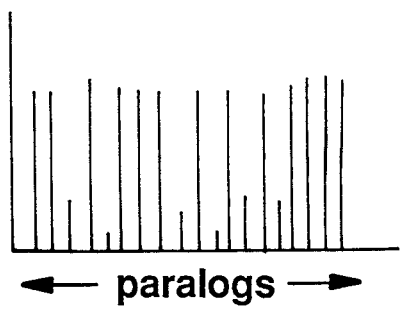
FIG. 3 shows the generic results of the corresponding assay of the same paralog panel with the labeled mixture in the presence of unlabeled analyte.

When it is confirmed that the labeled peptide mixture binds roughly equivalently to all candidate paralogs in the absence of analyte, or similar binding has been normalized, the screen is repeated in the presence of analyte. Those candidates which have specific affinity for analyte will show a decrease in the conjugation to labeled peptide mixture, the decrease being proportional to the specific affinity of the candidate for the analyte. A typical competition pattern is shown in FIG. 3. The meaning of the coordinates is the same as in the other figures. The paralogs with greatest affinity to the analyte, however, show the lowest levels of labeling as this indicates successful competition of the analyte with the labeled protein mixture for the paralog. By assessing the ability of the analyte to compete, those paralogs which show the greatest decrease in label uptake are selected as having the parameters that are most favorable for binding analyte.

The screening process can be repeated with additional panels having properties intermediate to those members which show the greatest specific affinity or the most desirable elution pattern behavior in the original panel, in order to fine-tune the molecular shape and charge distribution pattern of the ultimately chosen paralog. The screen can be repeated an arbitrary number of times with an arbitrary number of panels to the degree of specific affinity or the chromatographic behavior required. The electron cloud pattern of the paralog panel can thus be systematically manipulated to optimize the affinity of the paralog for the analyte; if the paralog will be used as an affinity ligand in a chromatographic procedure, an affinity that is so great that elution is difficult may not be desirable, and the correct pattern should be chosen. The effect of conformation control can also be studied, as described above.

Use of the Selected Paraloqs

For use in chromatography, when a paralog with satisfactory characteristics for a desired analyte is chosen, it is conjugated to a solid support using conventional means known in the art. Typical solid supports include polysaccharide supports, acrylamide gels, silica supports, alumina, and the like across the range of typical commercially available chromatography supports. A particularly favored type of support is a fluorocarbon polymer such as polyvinylidene difluoride (PVDF), for example that marketed by Millipore or Immobilon TM . A wide variety of conjugation techniques is also available including those which introduce a linking arm, if desired, between the solid support and the paralog ligand. The use of a linking arm of a length equivalent to about 3–9 carbons is advantageous in some instances in order to provide greater accessibility of the analyte to the ligand.

The resulting substrate, comprising solid support conjugated to a paralog specific for binding to the desired analyte, can then be used in a manner conventional for chromatographic substrates. It can be packed into columns or placed in filter beds to adsorb the analyte when the composition containing the analyte is contacted with the substrate. Since the paralog is a relatively stable ligand, preparations and columns packed with the invention substrate can be included in apparatus designed for HPLC.

The advantages of adapting affinity-based chromatography to HPLC cannot be easily overestimated, especially if the chromatographic procedure is conducted on a preparative scale. Resolution in preparative procedures needs to be achieved on the basis of the characteristics of the column rather than the brute force methods of increasing the size of the column or adjusting the strength of the eluant downward so that elution will take a longer time period. Any adjustment which increases the complexity or amount of eluting solvent is a serious drawback on a preparative scale. For example, expensive solvents and complex mixing protocols are reasonable when a total of 10–100 ml is required as in analytical procedures; they become expensive and problematical when hundreds of gallons are required as is often the case in preparative protocols. Not only does the solvent need to be recovered in order to lower the cost, an expensive process in itself, but it also needs to be removed from the product being prepared.

In addition, since material purified by preparative chromatography is generally required to be recycled through the column to effect adequate resolution, complex elution protocols have the additional disadvantage of requiring reequilibration of the column in the recycled phase.

For the foregoing reasons, in general, analytical procedures become scalable only when the basis for the separation is selectivity of the adsorbent—i.e., is based on an affinity chromatography approach.

In one particularly preferred protocol, a column can be constructed having a series of paralogs of varying, generally increasing, affinity for the target analyte. The succession of binding affinities as the analyte travels through the column is effective in improving resolution. In a typical embodiment, the column begins with a paralog ligand which has very low affinity for the target; the paralogs to follow have increasing affinity.

Accordingly, columns packed with substrate having paralog ligands can be used as either analytical or preparative tools, and the use of paralog-derivatized substrate columns provides a convenient and efficient alternative to more conventional chromatographic approaches. If the analyte is a drug, the paralog-derivatized substrate can be used as a specific reagent to adsorb the drug from body fluids and the drug can then be reeluted for analysis. If the analyte is a toxin appearing in waste products, the substrate can be used for detection, and also for removal of the toxin from the mixture. If the analyte is a desired product made in low yield, the substrate can be used to isolate the product batchwise or using standard chromatographic techniques.

Advantage can also be taken of those paralogs which have the property of specific affinity for toxins by using them as scavengers in vitro and in vivo. For example, in one embodiment, latex beads conjugated to paralog might be delivered to the intestines or the bloodstream as an antidote to poisoning. In another embodiment, such configurations might be used as delivery systems for drugs which bind specifically, but with moderate affinity to the paralog.

While the selected paralog has utility when conjugated to solid support, especially in chromatography, the utility of the paralog is not limited to its solid-bound form. The paralog of appropriate composition and characteristics can also be used to substitute for the corresponding antibody or fragment thereof in standard immunoassays. For use in this manner, the paralog may or may not be labeled, depending on the protocol. For example, in a typical sandwich assay, microtiter wells coated with paralog are used to test samples for antigen, wherein antigen bound to paralog is then labeled using the labeled form antibody specific for a different epitope or with the labeled form of an alternate paralog. Or, labeled paralog can be used to compete with any analyte antibody in a sample for antigen bound to solid substrate. As is well understood in the art, the variety of specific protocols for solid phase-based and agglutination-based immunoassays is vast and well understood by practitioners of the art.

The following examples are intended to illustrate but not to limit the invention.

EXAMPLE 1

Synthesis of a Paralog Panel

Figure 5:
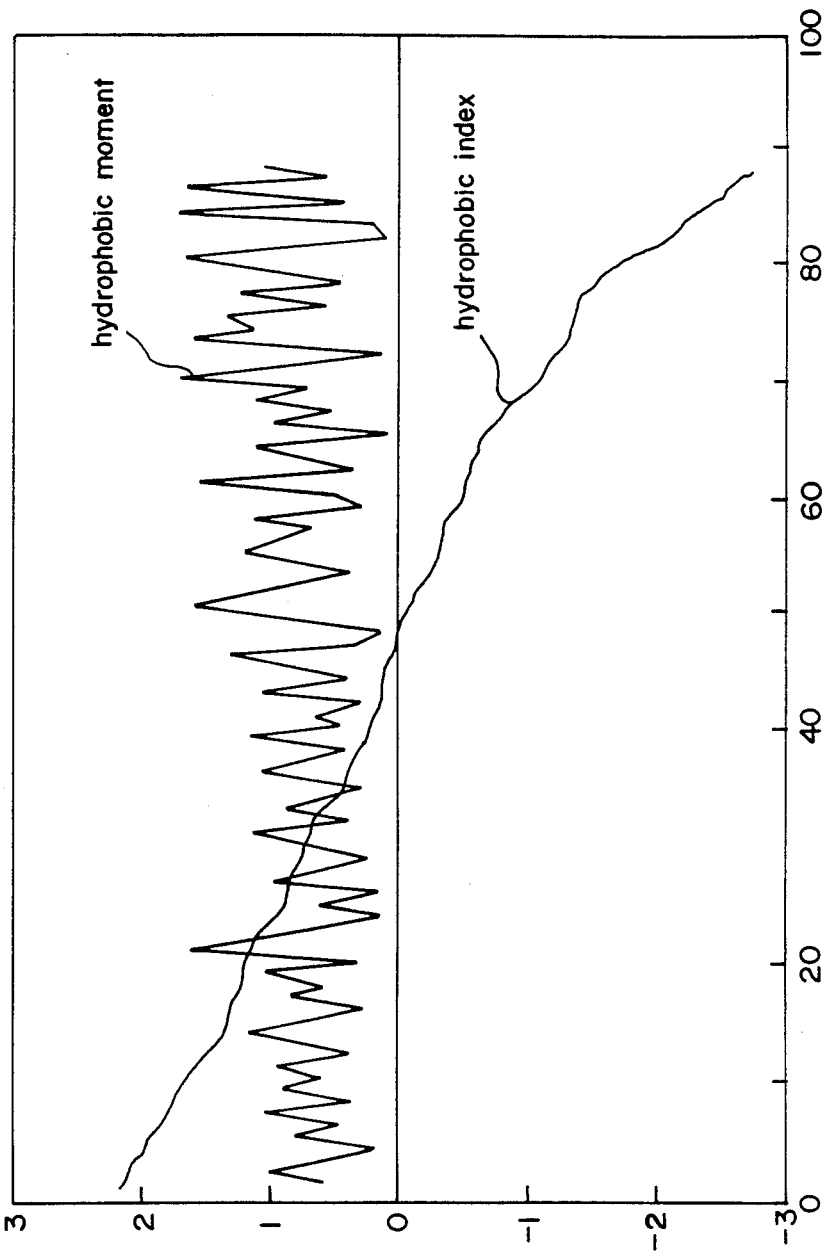
FIG. 5 shows the variation in hydrophobicity index and hydrophobic moment across the panel of FIG. 4.

A panel of 90 pentapeptides was designed on the basis of decreasing hydrophobicity and periodic variation of hydrophobic moment. FIG. 4 shows the list of pentapeptides synthesized numbered 1–88; FIG. 5 shows the hydrophobic index and the hydrophobic moments across this panel.

The panel was synthesized using the method of Geysen, H. M., et al, *Proc Natl Acad Sci USA* (1984)(supra). The remaining eight polyethylene pins were used for controls on the synthesis to be analyzed by amino acid analysis.

The set of polyethylene pins containing the paralog panel is then tested for uniform reaction with a mixture of proteins. The mixture is obtained by hydrolysis of yeast lysate using trypsin, and the resulting mixture is labeled by use of Bolton-Hunter reagent using 125-I as described above.

The labeled hydrolysate is used to treat all 90 panel members, and the amount of label bound detected. The amount of binding is quantitated by placing the treated pegs in contact with an X-ray film and detecting the density of the spots on the film, or by individually counting each bound peptide by removal of the pegs containing bound peptides and direct counting with a gamma counter to assess the amount of radioactivity on each peg corresponding to the supported paralogs.

The protein mixture is found to bind reasonably similarly to the members of the panel, and the binding values are normalized to 100%.

The panel is then retested by repeating the screen with the addition of a defined amount of analyte to the mixture in the microtiter wells. A small number of peptide-conjugated pins show greatly decreased labeling. These chosen peptides represent the result of an initial screen for molecules of suitable electron cloud patterns. If desired, further refinement for candidate peptides can be obtained through conformation control, testing under variable conditions as described above, and in addition, panels having slight variations of the properties of the best candidates can be prepared in a manner analogous to that described in this example.

When a reasonable number of successful candidate paralogs have been obtained, these successful candidate paralogs are synthesized using routine solid-phase methods in sufficient quantity to verify their sequence. If the paralog is to be used in chromatography, it can be attached to a solid support such as Affi-prep-10 (Bio-Rad) and packed into a chromatography column. Alternatively, the chromatographic support can be obtained by allowing the peptide to remain on the synthesis support such as the silica-based support, Ultra Affinity-ET TM (Beckman) upon which it was synthesized.

In order to verify that the paralog has the required specific affinity, a similar column can be prepared using a scrambled form of the paralog's amino acid sequence as ligand. The analyte will bind to the paralog-containing column, but not to the scrambled peptide-containing one. The Atassi references (supra) confirm that such scrambling destroys binding.

What is claimed is:

1. A method to identify a peptide having a sequence of 4–20 amino acids useful for the conduct of affinity chromatography with respect to an analyte,
   wherein said peptide has specific affinity for said analyte, which method comprises:
   screening, for ability to bind said analyte, a panel of individual candidate peptides wherein said candidate peptides have systematically varied values of at least two parameters selected from the group consisting of hydrophobic index, amphipathic characteristics, and charge pattern.

2. The method of claim 1 wherein the candidate peptides have sequences of 5–15 amino acids.

3. The method of claim 1 wherein said screening step is conducted by assessing the ability of analyte to compete with a labeled peptide mixture, which mixture is capable of binding to all candidate peptides of the panel, for binding to each candidate peptide in the panel.

4. The method of claim 3 wherein said peptide mixtures are labeled by iodinating acetylation.

5. The method of claim 1 wherein said two parameters are hydrophobicity and amphipatic characteristics.

6. The method of claim 1 wherein said two parameters are hydrophobicity and charge pattern.

7. The method of claim 1 wherein said two parameters are amphipatic characteristics and charge pattern.

* * * * *